(12) United States Patent
Sato

(10) Patent No.: US 7,347,163 B2
(45) Date of Patent: Mar. 25, 2008

(54) MICROBIAL FEEDSTOCK FOR FILTER FEEDING AQUATIC ORGANISMS

(76) Inventor: Gordon H. Sato, 27 Cedar St., Wenham, MA (US) 01984

( * ) Notice: Subject to any disclaimer, the term of this patent is extended or adjusted under 35 U.S.C. 154(b) by 150 days.

(21) Appl. No.: 10/536,506

(22) PCT Filed: Nov. 26, 2003

(86) PCT No.: PCT/US03/38197

§ 371 (c)(1),
(2), (4) Date: Apr. 3, 2006

(87) PCT Pub. No.: WO2004/047523

PCT Pub. Date: Jun. 10, 2004

(65) Prior Publication Data

US 2006/0185609 A1    Aug. 24, 2006

Related U.S. Application Data

(60) Provisional application No. 60/429,095, filed on Nov. 26, 2002.

(51) Int. Cl.
A01K 61/00 (2006.01)

(52) U.S. Cl. ..................... 119/212; 119/204

(58) Field of Classification Search .............. 119/212, 119/204, 205, 210
See application file for complete search history.

(56) References Cited

U.S. PATENT DOCUMENTS

| | | | |
|---|---|---|---|
| 3,576,643 A | 4/1971 | Ayukawa et al. | 99/2 |
| 3,604,395 A | 9/1971 | Huslin | 119/2 |
| 3,669,074 A | 6/1972 | Stasio | 119/2 |
| 3,673,986 A | 7/1972 | Braunhut | 119/2 |
| 3,738,316 A | 6/1973 | Stasio | 119/2 |
| 3,830,937 A | 8/1974 | Shigeno et al. | 426/2 |
| 3,939,279 A | 2/1976 | Kawano et al. | 426/2 |
| 4,080,930 A | 3/1978 | Pruder et al. | 119/4 |
| 4,368,691 A | 1/1983 | Brune | 119/2 |
| 4,449,480 A | 5/1984 | Ison et al. | 119/4 |
| 4,593,647 A | 6/1986 | Sorgeloos et al. | 119/2 |
| 4,640,227 A | 2/1987 | Blancheton et al. | 119/2 |
| 4,906,479 A | 3/1990 | Kitagawa et al. | 426/1 |
| 4,960,795 A | 10/1990 | Salte et al. | 514/560 |
| 5,104,668 A * | 4/1992 | Cole et al. | 426/285 |
| 5,377,624 A | 1/1995 | Craig et al. | 119/234 |
| 5,739,006 A * | 4/1998 | Abe et al. | 435/67 |
| 5,866,025 A | 2/1999 | Kataoka et al. | 249/114.1 |
| 5,894,936 A * | 4/1999 | Sanders et al. | 209/270 |
| 5,945,102 A | 8/1999 | de Faire et al. | 424/94.63 |
| 6,223,689 B1 | 5/2001 | Nelson | 119/234 |
| 6,615,767 B1 * | 9/2003 | Untermeyer et al. | 119/215 |
| 6,789,502 B2 * | 9/2004 | Hjaltason et al. | 119/51.04 |
| 6,851,387 B2 * | 2/2005 | Untermeyer et al. | 119/212 |
| 7,063,855 B2 * | 6/2006 | Hjaltason et al. | 424/283.1 |
| 2003/0154926 A1 * | 8/2003 | Untermeyer et al. | 119/215 |
| 2004/0107914 A1 * | 6/2004 | Untermeyer et al. | 119/215 |
| 2007/0224318 A1 * | 9/2007 | Grymonpre et al. | 426/392 |

FOREIGN PATENT DOCUMENTS

| | | |
|---|---|---|
| EP | 0 104 702 | 4/1984 |
| WO | WO 94/23569 | 10/1994 |

* cited by examiner

*Primary Examiner*—Yvonne R. Abbott
(74) *Attorney, Agent, or Firm*—John C. Serio; Seyfarth Shaw LLP

(57) ABSTRACT

The present invention provides a method of cultivating filter feeders such as Artemia by substituting special microorganisms for naturally occurring microscopic algae, and providing conditions optimal for the growth of these organisms. These subsituted special microorganisms provide an abundant food source for Artemia and subsequently the Artemia provide a food source for higher order members of the marine food chain.

23 Claims, No Drawings

MICROBIAL FEEDSTOCK FOR FILTER FEEDING AQUATIC ORGANISMS

CROSS REFERENCES TO RELATED APPLICATIONS

This application claims priority of the U.S. Provisional Patent Application Ser. No. 60/429,095 filed Nov. 26, 2002 which is incorporated by reference in its entirety.

FIELD OF INVENTION

This invention relates to a method of increasing the production of filter feeding organisms such as Artemia in aquaculture, these filter feeding organisms can be used as feed in the cultivation of farmed fish, crustaceans and shellfish.

BACKGROUND OF INVENTION

In recent years it has become increasing popular to cultivate marine species in controlled settings. This cultivation, which is commonly referred to as aquaculture, has allowed the production of a variety of marine species for human consumption. Increasingly, many edible fishes have been produced using aquaculture. While aquaculture has shown marked technological increases, to support the growth of this industry, it is necessary to produce an artificial feed or to increase the harvest of naturally occurring foodstuff such as Artemia, Brachinus salina, Daphnia, etc.

All marine life in the seas ultimately depends on microscopic algae for their growth or the growth of their food within the marine food chain. This microscopic algae, which is the first link within the marine food chain, is directly consumed by filter feeders such as shell fish, and indirectly through the complex food chain within the sea by the rest of marine life. Algae grows very slowly, however, as they only divide approximately once a day and therefore they are not easily available. This lack of availability contributes to a significant increase in the cost of aquaculture products.

Attempts to replicate or replace natural foodstuff within aquaculture have been met with limited success. In U.S. Pat. No. 5,158,788 to Lavens et al. ("Lavens"), a method is described to produce a feed for aquaculture from yeast. Lavens entails a multi-step process in which yeast cells are processed by hydrolyzing its cell wall producing a digestible feed for aquaculture. Unfortunately, the multi-step process as suggested by Lavens is labor intensive and therefore not feasible economically. Most importantly, the destruction of the cell wall that is needed to produce this artificial feed causes pollution of the aquaculture by the cell materials contained within the yeast cell.

One significant natural food source within the marine food chain that feeds off microscopic algae is Artemia. Artemia commonly referred to as brine shrimp is an excellent foodstuff for aquaculture, because of its position within the marine food chain and its desirability as a food source for higher members of marine culture. They are an excellent food for aquaculture, because unlike prior art foods in aquaculture they do not undergo putrefaction by microorganisms and foul water used in aquaculture, but rather they clear the water of fouling micro-organisms. It is commonly known that Artemia can be used as a feed for species such as shrimp, fishes, etc.

The natural harvesting of Artemia for their use in aquaculture, however, is subject to environmental factors that have recently led to shortages. Artemia grow in large saline lakes such as the Great Salt Lake in Utah. Artemia have been harvested in the Great Salt Lake for many years. Unfortunately, recent harvests have been poor and the cost of Artemia cysts has increased more than three fold. It is thought that these recent poor harvests have been caused by changing weather patterns. Severe climatic disturbances caused by the warm weather and excessive rainfall that accompanied El Nino caused production levels of the Artemia from the Great Salt Lake to decrease dramatically. The harvest of Artemia cysts in 1995-96 and 1996-97 was approximately 15 million pounds gross weight. Of this total harvest only about fifty percent is suitable for use. The 1997-98 harvest was only approximately 6 million pounds gross weight. Decreases in harvesting of Artemia cysts, such as in the case of El Nino, not only cause problems with availability, but also sharp increases in the price of Artemia cysts. This sharp increase in cost makes the use of Artemia as a feed for aquaculture economically impermissible.

Although there are several other sources of Artemia throughout the world, the Great Salt Lake provides more than ninety percent of the world's Aretmia cyst consumption. While additional sources of Artemia have been found in Russia, Turkey, and China, these additional sources have not offset the declining harvest of the Great Salt Lake. Various methods of producing Artemia within aquaculture have been explored such as in Vietnam, where Artemia have been growth in ponds having abundance of natural algae. In Hawaii, yeast and greenwater have been used to grow Artemia and rotifers for seahorse and Asian sea bass aquaculture. Unfortunately, these various efforts have been met with limited success as these prior methods of producing Artemia are labor extensive and not economically feasible.

SUMMARY OF INVENTION

The bulk of food for all living creatures of the sea originates with microscopic algae. This microscopic algae is directly consumed by filter feeders such as shellfish and indirectly by the rest of marine life through a complex food chain. The inventive method consists of mimicking this natural phenomenon in mariculture by substituting special microorganisms for naturally occurring microscopic algae, and providing conditions optimal for the growth of these organisms. These substituted special microorganisms then provide an abundant food source for higher order members of the marine food chain.

As stated above, microscopic algae grow very slowly and even when provided with all their mineral requirements, divide only about once every 24 hours. On the other hand, microorganisms such as bacteria, and probably certain species of algae, blue green bacteria, and fungi divide about once every thirty minutes if provided with an organic energy source. According to the inventive method, mineral elements are added to seawater to provide a culture for the optimal growth of selected microorganism.

The added mineral elements are nitrogen, phosphorus, and iron, because these are the only mineral elements deficient within seawater that are essential to all life. In addition to the added elements, sugar (sucrose) is added to provide an energy source. In an illustrative embodiment of the inventive method, sucrose is used to provide both energy and a carbon source. Sucrose has an advantage as an energy source, in that it consists of only carbon, oxygen, and hydrogen. Sucrose, however, is only one example of carbonaceous substances that can serve this function.

Other food sources can be used to support the growth of these special microorganisms that include such inexpensive products, such as peanut cake after the oil is pressed out, molasses, which is a by-product of sugar production, sugar beet syrup and cane syrup or the like. Their disadvantage is that they can support many kinds of microorganisms, some of which could be pathogenic. This disadvantage, however, can be remedied by sterilizing seawater with chlorine or filtering the seawater. Care has to be taken, however, to prevent foreign microbes' entry into the cultures. It is contemplated within the scope of the invention that the seawater within the culture medium can be refreshed frequently to prevent unwanted organisms from taking over the culture.

It is also contemplated within the scope of the invention that the inventive method can be used as an efficient method to fix atmospheric carbon dioxide. The fixing of atmospheric carbon dioxide into plant material requires a significant amount of energy. The use of the inventive method to grow shellfish on a large scale wherein the shellfish produce calcium carbonate from atmospheric carbon dioxide results in a more energy efficient method of alleviating the excess of carbon dioxide within the atmosphere.

DETAILED DESCRIPTION

The instant invention provides inventive methods for the growth of filter feeders such as Artemia using special microorganisms such as bacteria as a food source. It is contemplated within the scope of the invention that other filter feeders such as claims, oysters and scallops or the like. This growth of Artemia is accomplished with greater production and reliability of existing methods.

According to the inventive method, seawater is placed in culture tanks and fortified with nitrogen, phosphorus and iron, and sterilized with chlorine forming a culture medium. After the chlorine is dissipated, a sugar such as sucrose or the like and a dense culture of *Bacillus megatherium* or any other suitable organism is added to the culture medium. After the addition of the minerals and sugar and aeration of the culture, in approximately one-day, a dense bacterial culture is formed. Artemia cysts are added and they subsequently consume bacteria and grow. The overnight culture of *Bacillus megatherium* should have a volume of approximately 1/10,000 within the culture tank. Because the Artemia, which are filter feeders, thrive on the *Bacillus megatherium*, it is contemplated within the scope of this invention that other filter feeders such as clams, oysters or the like could also grow on this diet.

The culture medium is purposely simple and highly selective. Very few organisms can grow in the high salinity of seawater, and produce all their complex molecules when provided with only minerals and sugar. This simplicity of the culture medium makes it highly unlikely that the organisms would be pathogenic. This is borne out in experiments that are set forth below, where the only (predominant) bacterial organisms are *Bacillus megatherium* and *Vibrio alginolyticus*. Neither of these bacteria is considered pathogens although the *Vibrio* may be classified as an opportunistic pathogen. It is contemplated within the scope of this invention that any deleterious effects of unwanted organisms can be alleviated by using clonal strains of for example *Bacillus megatherium*. The *Bacillus* is a spore former so it would be relatively easy to maintain axenic or near axenic cultures.

In several experiments it was found that culture tanks turned dark green when sugar was added. This change in color indicates that algae or blue green algae exist within the culture medium and their growth is enhanced by sugar. Fungus has also been found within the culture that contains large quantities of the unsaturated fatty acids that are in short supply in mariculture. It is not known if the fungus can grow in this simple media.

One may find that selected special microorganisms are suitable in every respect except that they are difficult to digest. The selection of filter feeders such as Artemia or clams needs to take into account their ability to digest a selected special microorganism. It is contemplated within the scope of the invention that a naturally occurring special microorganism can be genetically altered to provide a more suitable food. This genetic alteration can be but not limited to increasing the content of unsaturated fatty acids.

The present invention will be described in more detail by way of examples; these examples should be construed as merely illustrative of the inventive method and should not be construed to be limited thereto.

EXAMPLE 1

To test the nutritional value of bacteria, and the procedure of culturing, the following experiment was done. Two 200-liter glass aquaria were set up out doors. The aquaria were partially shaded. The aquaria were filled with seawater from the Red Sea. On the first day, each aquarium received 10 mg of Artemia cysts from the Great Salt Lake, and iron EDTA, urea, and sodium dibasic phosphate. The final concentrations within the aquaria were as follows: ferric chloride 0.002 gms per liter, sodium EDTA 0.0035 gms per liter, sodium dibasic phosphate 0.0025 gms per liter, and urea 0.05 gms per liter. On day three, ten grams of sucrose were added to aquarium 1, and none to aquarium 2. On day 23, the Artemia were harvested with a fine aquarium net, daubed dry, and weighted. From tank 1 (with sugar) 27.0 grams of Artemia were harvested, and from tank 2 (without sugar) 3.0 grams of Artemia were harvested. The temperature during the time of the experiment ranged from approximately 25 to 36 degrees centigrade.

Approximately ten times as many Artemia were produced when sugar was provided as when no sugar was given. Some Artemia were produced in the absence of sugar because, without being bound to any particular theory, it is believed that in partial sun light algae were produced as food for the Artemia. The bulk of the food was sugar-generated bacteria. In this experiment one gram of sugar produced almost three grams of Artemia (wet weight).

As a result of this experiment, the production rate in ponds was calculated as follows; 27 grams per 200 liters per 23 days is equal to 27 grams per 200 liters per 23 days times 1000 liter per cubic meter or 5 times 27 grams per year, or 5 times 27 grams per cubic meter times 365/23 per year, or 5 times 27 grams per cubic meter times 10,000 cubic meter per hectare (one meter deep pond) times 365/23 per year divided by 1,000,000 grams per ton. This equals about 21 tons per hectare per year.

The experiment was started with Artemia cysts so the initial period is one of slow growth until the Artemia grow to adult size and start reproducing. In a commercial production, the growing population would be kept high with continuous partial harvesting at a controlled rate.

EXAMPLE 2

The next illustrative example was done indoors to control the temperature. With air conditioning the room temperature was maintained at approximately a constant 27 degrees centigrade. On day 1, each of three plastic buckets were set up with fifty liters each of sea water from the Red Sea. Each bucket received 60 mgms of Artemia cysts from the Great Salt Lake, and nitrogen, phosphorus, and iron as in the previous experiment. The buckets were aerated as in the previous experiment. On the second day, buckets 2, and 3 received 2.5 Gms of sucrose, and 50 ml of an overnight culture of bacteria. The bacterial culture was prepared by taking 500 ml of fresh sea water, and adding iron, nitrogen, and phosphorus as before and 0.2 gms of sugar per liter, and aerating overnight. Overnight the cultures became quite cloudy. On the $5^{th}$ day, bucket 3 received 2.5 Gms of sugar, and nitrogen, phosphorus and iron equivalent to what had been added initially. Bucket 3 also received 50 ml of bacterial culture. On the $9^{th}$ day and the $13^{th}$ day bucket 3 received nitrogen, phosphorus, and iron as previously, and 50 ml of bacterial culture. On day 9, and 13, only bucket 3 received sugar, which was 5 gems each day. On the $16^{th}$ day, Artemia were harvested and weighed.

Bucket 1 that received no sugar except for the small amount in the bacterial inoculum yielded no detectable Artemia. Bucket 2 that had received a total of 5.0 gms of sugar yielded 2.3 gms of Artemia and bucket 3 that had received a total of 15 gms of sugar yielded 16.8 gms of Artemia.

Again, when sugar is added to the culture medium, bacteria and Artemia grow. When less sugar is added less Artemia are produced. In an enclosed room without sunlight, no algae grow in the culture, and no Artemia are produced without sugar. Without being bound to any particular theory, it appears that Artemia grown with sugar but without sunlight do not reproduce. No offspring Artemia are observed, and the Artemia do not couple. This lessens the final yield because with sexual reproduction, the final yield would consist of the adults derived from the initial cyst input, but also their offspring.

The yield of Artemia per gram of sugar was a little more than one gram of Artemia (wet weight) per gram of sugar. The yield per hectare of pond one meter deep per year would be about fifty tons per hectare per year. This experiment was flawed in that bucket 3 differed from bucket 1 not only in that 3 received sugar and 1 did not, but that 3 also received extra minerals and bacteria inoculum and 1 did not. This was corrected in a further experiment that showed that the crucial factor is sugar.

EXAMPLE 3

A further illustrative example was undertaken with four plastic buckets with 50 liters each. Along with the sea water as noted above, nitrogen, phosphorus, iron and about 60 mgs of Artemia cysts were set up as in the previous illustrative examples. On the second day, buckets 2, 3 and 4 were given 2.5 Gms of sugar (10 ml of 0.25 Gms per cc in water). Also added to the buckets was 50 ml of overnight bacterial culture. On the $3^{rd}$ day, bucket 2 was illuminated with a 100 watt light bulb suspended about six inches above water surface. The light was kept on for the duration of the experiment. On the $5^{th}$ day, 2.5 gms of sucrose was added to buckets 2, 3 and 4. On the $5^{th}$ day, fifty ml of bacteria culture was added to all buckets. On the $9^{th}$ day, 2.5 Gms of sucrose were added to buckets 2, 3 and 4 and fifty ml of bacteria culture was also added to all buckets. On the $12^{th}$ day, 2.5 gms of sugar was added to buckets 2, 3 and 4 and all buckets received 50 ml of bacterial culture and nitrogen, phosphorus, and iron equivalent to what had been added initially.

On the $16^{th}$ day, Artemia were harvested and weighted. Bucket 1, which received no sugar, produced no detectable Artemia. Bucket 2, which had received 10 Gms of sugar, and light, produced 7.97 Gms of Artemia. Bucket 3, which had received 10 gms of sugar and no light produced 6.08 gms of Artemia. Bucket 4 was not harvested because the air pump failed and all the Artemia were dead.

When sugar is added to the culture medium, bacteria and Artemia grow. Without sugar and no sunlight, no Artemia are produced. With some light from a hundred-watt bulb, more Artemia are produced than without light. The light bulb provides much less light than the full spectrum of natural sunlight. It is contemplated within the scope of the invention that production runs will be done outdoors so that sunlight will have a strong positive effect. It is not known whether the effect of light is due to light itself or to the small production of algae. In this illustrative example approximately 0.8 Gms of Artemia were obtained per gm of sugar.

EXAMPLE 4

An additional illustrative example was done with plastic tubs outdoors in the shade. On day 1, 3 plastic tubs were each filled with 20 liters of seawater, and the minerals nitrogen, phosphorus and iron as before. Each tub received about 24 mgs of Artemia cysts. The tubs were aerated. On days 2, 5, 9, 12 and 14, one gm of sucrose was added to tubs 1 and 2. On the same days that sucrose was added 20 ml of bacteria culture was added to all three tubs. On day 18, the Artemia were harvested and weighed. Tub 1 produced 2.12 gms of artemia, tub 2 produced 2.20 gms, and tub 3 which received no sugar produced 0.15 gms. Without being bound to any particular theory, it is believed that the yield was low because of the elevated temperatures, but clearly sugar is important. More than ten times as much Artemia were produced with sugar than without.

EXAMPLE 5

In a further illustrative example, seawater was obtained from Honolulu Harbor in an area adjacent to the experimental site and placed within a container. Sucrose was added to the seawater in the concentration of approximately 100 mg per liter. Also added to the seawater were inorganics such as urea, sodium phosphate, EDTA and $FeCl_3$ in concentrations of approximately 50 mg per liter. The container was sealed and air was blown into it though a glass plug. In approximately two days a dense bloom of bacteria occurred. The bacteria within the culture were primarily pleiotrophic rods, however, there was also some fast swimming bacteria. This bacterial culture comprised of "wild saltwater bacteria" (WSB) was the starter bacterial culture for this example.

A large tank trial was conducted at the research center in a large polyethylene tank within approximately 5000 liters of seawater. The tank was located outdoors and partially shaded. The tank was aerated and had a water temperature of ranging approximately between 28 to 29 degrees Centigrade. The tank was sterilized by the addition of 6% hypochlorite (i.e. clorox). For every 1000 liters of seawater about 750 ml of 6% hypochlorite was added. The hypochlorite was allowed to naturally dissipate with aeration over approximately one day. After the hypochlorite dissipated from the tank approximately 60 Gms of artemia cysts were added. On the following day (day 2) and on days 5, 7, 9 and 11 a 1:000 dilution of bacteria, inorganics and sucrose were added.

On day 12 the tank was harvested. Although survival from cyst to adult was only about 7 percent, the total yield of approximately 3031 Gms of artemia from approximately 60 Gms of cysts was significant. The final Artemia density was approximately 0.6 Gms per liter or approximately one artemia for every 4 ml of seawater. As the growth of Artemia within the tank was good and bacteria were being rapidly cleared from the water more concentrated dilution of bacteria were used on days 5 and 7 (1:250 dilution of bacteria) and on days 9 and 11 (1:125 dilution of bacteria).

EXAMPLE 6

In yet, a further illustrative example, seawater was again obtained from Honolulu Harbor in an area adjacent to the experimental site and placed within a container. Sucrose was added to the seawater in the concentration of approximately 100 mg per liter. Also added to the seawater were inorganics such as urea, sodium phosphate, EDTA and $FeCl_3$ in concentrations of approximately 50 mg per liter. The container was sealed and air was blown into it though a glass plug. In approximately two days a dense bloom of bacteria occurred. The bacteria within the culture were primarily pleiotrophic rods, however, there were also some fast swimming bacteria. This bacterial culture comprised of WSB was the starter bacterial culture for this work.

This illustrative example was conducted in one liter of autoclaved seawater in a two liter flask containing inorganics and sucrose at the above concentrations. The two liter flask was kept in indoors and covered at all times. The flask was constantly aerated and isolated from the outside with an air blanket and the temperature was maintained at approximately 23 degrees Centigrade. On the first day 6 mgs of Artemia cysts were added to the flask. On the second day and on the $5^{th}$, $7^{th}$, $9^{th}$, and $11^{th}$ day 1:1000 dilution of wild saltwater bacteria and sucrose were added. As the Artemia were growing rapidly and eating the bacteria the added bacteria was in the lesser dilution of 1:100 and additional feedings of bacteria were done on the $10^{th}$ and $12^{th}$ day in addition to the above feedings.

On the $13^{th}$ day the flask was harvested. The total yield of the flask was approximately 2.3 Gms of artemia from approximately 6 mgms of cysts. The final artemia density was approximately 2.3 gms per liter or approximately. The 2.3 Gms of artemia that were produced consume approximately 1.2 Gms of sucrose in the 13 days of growth. The hatching and survival rate of artemia was approximately 54 percent and average sizes of artemia were unusually large.

Although the illustrative embodiments of the invention suggest the use of the Artemia as a feedstuff, it will be appreciated by those skilled in the art that these Artemia may be used alone or in combination with other filter feeders grown according to the inventive method or in an admixture with conventional feedstuffs.

Although the illustrative embodiments of the invention suggest the use of the Artemia as a filter feeder, it will be appreciated by those skilled in the art that other filter feeders such as clams and mollusk may be used.

Although the illustrative embodiments of the invention suggest the use of bacteria as special microorganisms, it will be appreciated by those skilled in the art that other microorganism that will multiple in the culture medium may be used.

Although the invention has been shown and described with respect to exemplary embodiments thereof, various other changes, omissions and additions in the form and detail thereof may be made therein without departing form the spirit and scope of the invention.

What is claimed is:

1. A method for cultivating filter feeders comprising the steps of:

providing tanks with seawater having microorganisms;
    adding essential elements to said seawater;
    adding a food source to said seawater forming a mixture and aerating said mixture continuously thereby forming a dense bloom of bacterial; and
    adding artemia cysts to said mixture.

2. The method according to claim 1 wherein said essential elements are selected from the group consisting of nitrogen, iron and phosphorous.

3. The method according to claim 1 wherein said microorganisms are bacteria selected from the group consisting of *Bacillus megatherium* and *Vibric alginolyticus*.

4. The method according to claim 3 wherein said bacteria are genetically engineered to promote additional nutritional properties.

5. The method according to claim 3 wherein said bacteria are clonal bacteria selected from the group consisting of *Bacillus megatherium* and *Vibrio alginolyticus*.

6. The method according to claim 1 wherein said microorganisms are wild saltwater bacteria.

7. The method according to claim 1 wherein said food source is sucrose.

8. The method according to claim 1 wherein said food source is selected from the group consisting of molasses, peanut cake, sugar cane syrup and sugar beet syrup.

9. The method according to claim 1 wherein said filter feeders are Artemia.

10. The method according to claim 9 further comprising the step of harvesting adult Artemia from said seawater.

11. A method of preparing food for larvae of fish or crustacean, whereby nauplii released by the development of Artemia cysts or deposited by ovoviviparous reproduction are fed to said larvae comprising the production of Artemia cysts or Artemia nauplii according to the method of claim 9.

12. The method according to claim 11 wherein said Artemia cysts are fed to said larvae in an admixture of other feedstock.

13. The method according to claim 11 wherein said Artemia cysts are fed to clams, oysters, mullet, milk fish and mollusks.

14. The method according to claim 1 wherein said filter feeders are selected from the group consisting of clams and mollusk.

15. The method according to claim 14 wherein said disinfection step comprises the addition of chlorine to said seawater.

16. The method according to claim 1 further comprising the step of disinfecting said seawater.

17. The method according to claim 16 wherein said disinfection step comprises autoclaving said seawater.

18. The method according to claim 16 wherein said disinfection step comprises filtering said seawater.

19. The method according to claim 1 further comprising the step of exchanging said seawater to prevent unwanted organism.

20. The method according to claim 1 wherein said microorganisms are selected from the group consisting of algae and blue green algae.

21. The method according to claim 1 further comprising the step of providing light exposure to said tank.

22. The method according to claim 21 wherein said light is selected from the group consisting of natural sunlight and artificial light.

23. The method according to claim 1 further comprising controlling temperature of said seawater.

* * * * *